United States Patent [19]

Holcomb

[11] Patent Number: 5,599,531
[45] Date of Patent: Feb. 4, 1997

[54] HAIR CARE, HYDRATING, COLORING, AND PERMING COMPOSITIONS AND METHODS

[75] Inventor: Robert R. Holcomb, Hackleburg, Ala.

[73] Assignee: Novatech, Inc., Nashville, Tenn.

[21] Appl. No.: 113,795

[22] Filed: Aug. 27, 1993

Related U.S. Application Data

[63] Continuation-in-part of Ser. No. 76,349, Jun. 11, 1993.

[51] Int. Cl.$^6$ .............................. A61K 9/14; A61K 33/00
[52] U.S. Cl. ..................... 424/70.1; 424/70.2; 424/724
[58] Field of Search ................................. 8/444, 632, 649; 424/70, 724, 62, 70.1, 70.2

[56] References Cited

U.S. PATENT DOCUMENTS

| | | | |
|---|---|---|---|
| 4,000,317 | 12/1976 | Menda et al. | 424/357 |
| 4,089,997 | 5/1978 | Van Paesschen et al. | 427/171 |
| 4,330,291 | 5/1982 | Bugaut et al. | 8/406 |
| 4,764,363 | 8/1988 | Bolich, Jr. | 424/47 |
| 4,978,437 | 12/1990 | Wirz | 204/192.23 |
| 5,298,792 | 3/1994 | Manning | 257/758 |

OTHER PUBLICATIONS

Iler, "The Chemistry of Silica", John Wiley, pp. 354–365 (1979).

*Primary Examiner*—Jeffrey C. Mullis
*Attorney, Agent, or Firm*—Mallinckrodt & Mallinckrodt

[57] ABSTRACT

The penetration or absorption of water, oils, collagen, and other materials into the hair is greatly increased by adding a small quantity of inorganic charged colloidal silica to provide an aqueous suspension of the charged colloidal silica particles along with the material to be absorbed into the hair. In coloring hair, dye components can be absorbed into the hair without the use of alkaline solutions which damage the hair, and in perming hair, the disulfide bonds in the hair can be broken by tension caused by swelling due to water absorption in the hair, again without the use of damaging alkaline solutions. It is believed that the porosity and stable hydration of the hair can be varied through altering the electrostatic charge on the hair. The aqueous suspension of charged silica particles applied to the hair appears to alter this charge.

21 Claims, No Drawings

HAIR CARE, HYDRATING, COLORING, AND PERMING COMPOSITIONS AND METHODS

This is a continuation-in-part of application Ser. No. 08/076,349 filed Jun. 11, 1993 entitled "Body Care Compositions, Method of Using Same, and Method of Generating A Relatively Stable Aqueous Suspension of Colloidal Silica for Use Therein."

BACKGROUND OF THE INVENTION

1. Field

The present invention relates to hair care compositions of matter such as moisturizers, shampoos, conditioners, coloring agents, permanents, and body giving compositions, and to methods utilizing such compositions.

2. State of the Art

In today's market, it is estimated that approximately forty percent (40%) of the population of the United States utilizes some method of hair coloring and probably a like percentage use some products for permanents, waves or straightening the hair. In using traditional techniques, each time the hair is treated, its structure is altered and usually altered in a fashion that is detrimental to the hair shaft.

Traditional technology in dealing with hair coloring, conditioning and perming introduces destructive change into the various components of the hair, i.e., the cuticle, the cortex, and the medulla. The cuticle is composed of a layer of flattened, horny scales made up of keratinized protein. These scales overlap and move over one another to provide a flexible protection, like an armor covering of the hair shaft. Current technology requires use of an alkaline substance which hydrolyzes the scales, which causes them to swell and raise from the hair shaft. Normal procedure then utilizes an acid rinse to stop the alkaline hydrolysis process. The cortex portion of the hair shaft is made up of intertwined molecules of keratin protein. Processing of the hair in alkaline solutions induces softening of keratin through hydrolysis and reduction of strong disulfide bonds. The central portion of the hair fiber is known as the medulla and is composed of soft keratin. The cortex is probably the most important portion of the hair structure as it relates to coloring or perming of the hair.

At the current time, all processing of the hair for coloring or permanents is a result of an alkaline hydrolysis. Alkaline solutions disrupt the cuticular layer and allow penetration of water which causes swelling of the hair. The enlarged pores in the cuticle will allow dye components in aqueous solution to penetrate the hair cuticle. These dye particles can then be trapped inside the cortex of the hair by oxidation and condensation. This imparts a permanent color to the hair.

Current technology for permanent hair coloring is based upon oxidation procedure requiring the use of a peroxide. Initial application of an alkaline solution to the hair causes the disulfide bonds of the protein matrix to be altered or broken. The molecules of the dye components are of sufficiently small molecular size to penetrate the hair cuticle when it is opened by use of an alkaline solution. This allows water and the small dye components to be carried into the hair shaft itself. A peroxide solution is then applied to the hair and penetrates into the hair shaft to oxidize these dye components and cause them to become enlarged and produce color. The enlargement of the dye components upon oxidation traps them in the hair. This is then followed by an acid rinse or conditioning to counteract the action of the alkaline solution and stop its further damaging action to the hair. Even with the acid rinse, however, the alkaline environment is very damaging to the hair shaft. The hair and the hair proteins are resistant to weak acids. It would be far more desirable to carry out the hair coloring in an acid solution or a neutral pH solution. However, currently known procedures do not allow the use of an acid solution for relatively permanent hair coloring since it will not allow the penetration into the hair shaft or the break down of disulfide bonds. Acid hair coloring compositions are currently available, but the coloring is surface based and usually lasts for only a matter of weeks.

Perming is a two step process. Step one uses an alkaline solution to break the disulfide bonds in the hair cuticle and step two rejoins them in a new position. Different perm formulas break disulfide bonds in different ways. In cold waves, the reforming lotion does the work. In heat activated perms, heat and tension are required in addition to the reforming lotion. In both cases, the reduction process softens the protein and allows it to assume the shape of the curler. The final step in every perm is to saturate the hair with a chemical oxidizing agent, called a neutralizer. Again, the alkaline used to break the disulfide bonds can do significant damage to the hair.

SUMMARY OF THE INVENTION

I have discovered that an aqueous composition containing small quantities of an inorganic colloidal silica (preferably specially processed as described in my copending application Ser. No. 076,349 to provide a stable, active configuration) greatly enhances the penetration of water, oils, and collagen into a hair shaft. With enhanced penetration into the hair, hair coloring material penetrates the hair shafts to provide brighter color and longer retention of the color in the hair, and water or perming compositions penetrate into the hair shafts, all without use of alkaline chemicals which can damage the hair, and which are required in the prior art. The colloidal silica composition can be neutral or weakly acidic so as not to cause damage to the hair.

The inorganic colloidal silica can be beneficially used in a wide variety of hair care compositions such as in shampoos, conditioners, styling gels, styling mists, hair coloring preparations, and as an ingredient for perming composition and to activate the perms. The composition will allow water to penetrate into the hair shafts causing them to swell and breaking the disulfide bonds. Upon drying, the bonds will be reformed to provide curls or straightening depending upon the configuration of the hair during drying and reestablishment of the bonds.

The active component of the invention comprises an aqueous suspension of colloidal silica particles, preferably an aqueous solution with silica suspended therein. The silicon particles are preferably from about 10 to about 100 angstroms in size and have an electrical charge thereon. The solution is preferably mixed in such a way that the colloidal particles become electrically charged, preferably by circulation of the solution through a magnetic field, and further, that the solution pass through a magnetic void during mixing so that the charged particles assume a stable configuration in relation to internal bonding. The charge on the colloidal particles is stabilized to remain during a relatively long shelf life of the final product by the mixing process and by the addition of molar amounts of citrate or citrate salts. The colloidal particles are also believed to carry several layers of water bound to the particle.

In one aspect of the invention, the invention comprises a hydration-enhancing composition of matter containing a unique blend of an inorganic colloidal silica in combination with a usual hair coloring agent. The final hair coloring compositions of the invention preferably contain colloidal silica in a concentration from about 1 part per million [ppm] to about 50 parts per million [ppm]. However, greater concentrations of colloidal silica are also equally effective, and lesser concentrations may be effective in many applications.

In another aspect of the invention, an aqueous suspension of colloidal silica is used in perming the hair. The hair is rolled tightly on rollers or other forms and the solution of the invention is applied thereto. This causes the hair to swell and break the disulfide bonds therein. These bonds are reestablished upon drying of the hair on the rollers or other forms so the hair takes the new form as with prior art chemical perms.

The aqueous colloidal silica solution of the invention is a potent conductor of charge. When applied to the hair it varies the normal electrostatic fields on the hair shafts and allows current flow on the hair cortex and the hair surface. It is believed that this manipulation of the normal electrostatic field of the hair and the current flow helps in the effectiveness of the hair perming and hair coloring processes.

The invention also includes the method of applying an aqueous solution of colloidal silica as part of a hair coloring or hair perming procedure.

DETAILED DESCRIPTION OF THE ILLUSTRATED EMBODIMENT

Enhanced hair care compositions can be formulated by adding an aqueous suspension of colloidal silica to an existing hair care composition such as a shampoo, hair conditioner, hair coloring solution, or hair permanent solution to bring the concentration of colloidal silica within the composition to a preferred range of from about 1 ppm to about 50 ppm. The hair care product, particularly a shampoo or conditioner, is then used in a normal manner, but it has been found that such product is more effective than the product without the colloidal silica added thereto. The presence of the colloidal silica in the product appears to dramatically increase the ability of the product to penetrate into the hair. Thus, the product and the water, oils, and collagen therein, if present, will actually penetrate into the hair to provide moisturization and body. The result with such hair care products is to decrease drying and maintain body and managability of the hair. With hair coloring products the result is to provide deeper and more lasting color since the color components better penetrate the hair itself, and with both hair coloring and hair perming products to allow effective coloring or perming of the hair without damaging the hair through use of alkaline solutions.

The aqueous suspension of colloidal silica preferably takes the form of a solution to be added in small amounts to hair care compositions or used as part of the hair coloring or perming process and is preferably prepared in such a way that the colloidal particles become charged (it is believed that the particles take on a net negative charge) and assume an active configuration and the charge and configuration is stabilized so that the particles remain charged and remain in suspension during a relatively long shelf life of the solution and a relatively long shelf life of any products made using the solution. The particles and solution may be stabilized by adding citric acid (tripotassium salt) to the solution containing the particles and pH adjusted with acetic acid so it will also contain traces of citrate and acetate. In a preferred form of the invention, the solution contains about 500 PPM colloidal silica, 0.001 moles/liter of potassium citrate, and traces of acetate, in purified distilled water. This aqueous solution may be added in very small amounts to hair care compositions or diluted and used as a solution itself in perming procedures.

To prepare the inventive composition, as an example, an aqueous solution of colloidal silicon dioxide is first made up. This can be done by starting with a solution that is about 27% silicon dioxide in about 3 to about 4 molar NaOH. As one option, it has been found that citric acid or citric acid salts added in molar amounts about equal to the molarity of the NaOH improve the stability of the end solution. The starting solution and citric acid or citric acid salts, if present, is diluted very slowly, with stirring. Preferably, this is done over a period of several hours. Next, the solution is very slowly titrated with about 0.5–1.0 molar of an acid, usually hydrochloric or acetic acid, to a pH of between about 7.6 and 8.2. Again, this is preferably done over a period of several hours with constant stirring. The final concentration is a solution of preferably about 0.050% (about 500 parts per million) colloidal silica. At this time the silica is present as colloidal particles of between about 10 to 100 angstroms in size.

The nature of the silicate solution is described in more detail in my referenced copending application Ser. No. 076,349.

In order to generate a charge on the silica particles, it is preferred that during the mixing of the colloidal silica solution the solution be circulated through a magnetic field so that movement of the silica particles through the magnetic field generates the electrical charge on the silica particles. If the silica particles are passed through a magnetic field so as to cut through the lines of flux of the field, an electrical charge is generated on the particles as they cut through the lines of flux. The particles act as both a conductor and a capacitor, i.e., they generate a charge and store the charge. After passing through a magnetic field to generate a charge on the silica particles, it is preferred that the particles be passed through a space substantially void of any magnetic fields. This space allows each of the charged particles to then assume a configuration based on the charges on the particle and the internal bonding of the particle without regard to external fields. It is believed that this provides formation of a very stable colloidal particle. Circulation through the magnetic field and the magnetic void preferably takes place on a repetitive basis during generation of the colloidal solution. It has been found that with circulation through a magnetic field, the silica particles take on a net negative electrical charge.

Apparatus which has been found advantageous for mixing the colloidal solution is shown in my referenced copending application.

With hair coloring products, it has been found that the silica solution of the invention can be mixed with the dye components and that the dye components are then absorbed through the hair cuticle into the hair similarly as if the hair had been first treated with the usual alkaline solution. However, use of the alkaline solution is completely avoided. After absorption of the dye components into the hair, the hair is treated with an oxidizer, usually a peroxide solution, such as a weakly acidic or neutral hydrogen peroxide solution, which causes oxidation of the dye components in the normal manner. Since an alkaline solution has not been used, the acid rinse or conditioning to stop the action of the alkaline solution is not necessary, however a rinse or conditioning will usually be performed after use of the oxidizing solution.

All biological organisms are permanently located in an atmospheric electrostatic field that varies according to atmospheric conditions (between 100–1000 V/M). Through direct frictional contact, the hair can pick up charge and generate its own electric field. The anatomy of the hair is very similar to a lightening rod (sharp tip), it enables the charged shaft of hair to generate a high electric field. The tip of the hair shaft carries a positive charge while the portion of the hair shaft near the scalp carries a negative charge. Due to the high resistance of normal skin and hair, no compensating charge is supplied to the hair through the skin. This means that hair can stay charged for extended periods of time. The colloidal silica solution of the invention provides a hydrophilic, charged, and highly conductive medium, and allows constant current flow in the hair. This postulated current flow in the hair may ultimately explain operation of the invention.

It is believed that the colloidal silica solution provides highly charged conductive material in the form of the charged silica particles which adhere to the hair shaft and carry color into the shaft. By using the highly charged solution, it neutralizes the charge on the hair shaft by allowing electrostatic discharge. The discharge of the electrostatic charge allows this shell of hydration to be taken into the hair shaft without damaging the hair, most likely by iontophoresis. It will also carry with it the hair color, which, when in the hair, can then be oxidized in the same fashion as current technology provides.

Experimentation to date suggests that it is possible to alter the porosity and stable hydration of hair at neutral or acidic pH by altering the electrostatic charge on the hair. This is done by applying the highly conductive solution of colloidal silica to the hair. The solution is hydrophilic and bonds readily to the hair. This conductive solution, which is natural and non-toxic, allows constant current flow in the hair matrix and structurally alters the hair due to alteration in bonding between the helixes. This causes changes in permeability to small particles and water, possibly by the process of iontophoresis. This allows penetration of water, dye components, or other material into the hair.

In the perming of hair, i.e., causing substantially permanent changes in the structure of the hair, it has been found that if the hair is secured to a form, such as a curler, and is then treated with the aqueous silica solution of the invention, the hair will absorb large amounts of water without chemical damage. The absorption of water causes the hair to swell. In swelling, the disulfide bonds are broken due to tension on the bonds. The hair is then dried which reestablishes the disulfide bonds, but the bonds are rearranged from when they were broken so that the hair substantially peremanently takes on the configuration of the form, e.g., the curl of the curler.

In one example of a perming process, hair is tightly wrapped on a roller. It is then treated with a solution of 0.01 m acetic acid, collagen and colloidal silica in a concentration of 50 ppm. The hair is dried with a conventional hair drier to repair the bonding linkage. If desired, stabilizers may also be used along with drying to repair the bonding linkage. The results of perming in this manner appear to be comparable to the currently used chemical perming processes. However, since there is no chemical damage to the hair, repeated permanents can be given without accumulating trauma to the hair.

With use of the colloidal silica solution of the invention various hair coloring and hair perming and curling processes can be used.

As apparent from the above description, the invention provides a method of increasing the absorption of water or water with other materials, such as dye components, into hair by applying an aqueous solution or suspension of charged colloidal silica particles along with the other material to be absorbed into the hair. Where water is to be absorbed, the aqueous suspension of charged colloidal silica particles provides the water. Where material in addition to water is to be absorbed, the material may be included as part of the aqueous suspension, or the aqueous suspension may be added to the material, and then applied to the hair, or the aqueous suspension of silica particles may be applied to the hair either before or after application of the other material so that it mixes on the hair.

Whereas this invention is here described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A method of increasing the absorption of water into the hair comprising the step of applying to the hair an aqueous suspension of charged colloidal particles, wherein the aqueous suspension is generated by lowering the pH of an alkaline silica solution during circulation of the solution through a magnetic field greater than the earth's magnetic field to form charged colloidal silica particles in the solution of from 10 to 100 Angstrom in size.

2. A method of increasing the absorption of water into the hair according to claim 1, and of increasing the absorption of additional material into the hair, comprising the additional step of adding the additional material to be absorbed to the aqueous suspension of charged colloidal silica particles so that the additional material is absorbed into the hair with the water.

3. A method of increasing the absorption of water and additional material into the hair according to claim 2, wherein the additional material includes hair coloring dye components.

4. A method of increasing the absorption of water into the hair according to claim 1, wherein the colloidal suspension applied to the hair also changes the electrostatic charge on the hair.

5. A method of increasing the absorption of water into the hair according to claim 1, wherein the aqueous suspension of charged colloidal silica particles and has a concentration of colloidal silica particles of between 1 ppm and 50 ppm.

6. A method of coloring hair comprising the steps of separately applying an aqueous suspension of charged colloidal silica particles generated by combining over a period of time a solution of silica in about 3 to about 4 molar NaOH with water to a final concentration of the combination of about 0.05% silica while continuously circulating the combination through a magnetic field greater than the earth's magnetic field and titrating the combination with an acid to a pH of between about 7.6 and 8.2 to the hair and applying hair coloring dye components to the hair so that the dye components mix with the colloidal silica suspension on the hair and are absorbed into the hair; and thereafter applying an oxidizing solution to the hair to oxidize the dye components in the hair.

7. A method of coloring hair according to claim 6, wherein the dye components are applied to the hair after application of the colloidal silica suspension so that the dye components mix with the colloidal silica suspension on the hair.

8. A method of coloring hair according to claim 6, wherein the dye components are applied to the hair followed by application of the colloidal silica suspension so that the dye components mix with the colloidal silica suspension on the hair.

9. A method of coloring hair comprising the steps of applying a mixture of an aqueous suspension of charged colloidal silica particles generated by combining over a period of time a solution of silica in about 3 to about 4 molar NaOH with water to a final concentration of the combination of about 0.05% silica while continuously circulating the combination through a magnetic field greater than the earth's magnetic field and titrating the combination with an acid to a pH of between about 7.6 and 8.2 and hair coloring dye components to the hair whereby the dye components are absorbed into the hair; and thereafter applying an oxidizing solution to the hair to oxidize the dye components in the hair.

10. A method of coloring hair according to claim 9, wherein the dilution step and the titration step were each carried out over a period of time of several hours.

11. A method of coloring hair according to claim 9, wherein the aqueous suspension has been circulated through the magnetic field in a helical coil.

12. A method of coloring hair according to claim 11, wherein the aqueous suspension includes about 0.001 moles per liter of potassium citrate.

13. A method of coloring hair according to claim 9, wherein the mixture of the aqueous suspension of charged colloidal silica particles and hair coloring dye components has a concentration of colloidal silica particles of between 1 ppm and 50 ppm.

14. A method of coloring hair comprising the steps of applying a mixture of an aqueous suspension of charged colloidal silica particles generated by lowering the pH of an alkaline silica solution during circulation of the solution through a magnetic field greater than the earth's magnetic field to form charged colloidal silica particles in the solution of from 10 to 100 Angstroms in size and hair coloring dye components to the hair whereby the dye components are absorbed into the hair; and thereafter applying an oxidizing solution to the hair to oxidize dye components in the hair.

15. A method of perming hair, comprising the steps of placing the hair on a form; applying an aqueous suspension of charged colloidal silica particles to the hair on the form, said aqueous suspension of colloidal silica particles having been generated by lowering the pH of an alkaline silica solution during circulation of the solution through a magnetic field greater than the earth's magnetic field to form charged colloidal silica particles in the solution of from 10 to 100 Angstroms in size; allowing water from the colloidal suspension of silica to be absorbed by the hair causing the hair to swell and break the disulfide bonds in the hair; drying the hair to reestablish the disulfide bonds in the hair on the form so as to conform the hair to the form.

16. A method of perming hair according to claim 15, wherein the form is a roller.

17. A method of perming hair according to claim 15, additionally including the step of applying a stabilizer to the hair during drying to help reestablish the disulfide bonds.

18. A method of perming hair, comprising the steps of placing the hair on a form; applying an aqueous suspension of charged colloidal silica particles to the hair on the form, said aqueous suspension of colloidal silica particles having been generated by combining over a period of time a solution of silica in about 3 to about 4 molar NaOH with water to a final concentration of the combination of about 0.05% silica while continuously circulating the combination through a magnetic field greater than the earth's magnetic field and titrating the combination with an acid to a pH of between about 7.6 and 8.2; allowing water from the colloidal suspension of silica to be absorbed by the hair causing the hair to swell and break the disulfide bonds in the hair; drying the hair to reestablish the disulfide bonds in the hair on the form so as to conform the hair to the form.

19. A method of perming hair according to claim 18, wherein the form is a roller.

20. A method of perming hair according to claim 18, additionally including the step of applying a stabilizer to the hair during drying to help reestablish the disulfide bonds.

21. A method of increasing the absorption of water into the hair according to claim 1, wherein the aqueous suspension has been circulated through the magnetic field in a helical coil.

* * * * *